(12) United States Patent
Nguyen et al.

(10) Patent No.: US 11,911,218 B2
(45) Date of Patent: Feb. 27, 2024

(54) TWO DIMENSIONAL ULTRASONIC ARRAY TRANSDUCER WITH ONE DIMENSIONAL PATCHES

(71) Applicant: KONINKLIJKE PHILIPS N.V., Eindhoven (NL)

(72) Inventors: Man Nguyen, Cambridge, MA (US); Jean-Luc Robert, Cambridge, MA (US); Ramon Quido Erkamp, Cambridge, MA (US); Sheng-Wen Huang, Cambridge, MA (US); Bernard Joseph Savord, Andover, MA (US); Emil George Radulescu, Ossining, NY (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 1219 days.

(21) Appl. No.: 16/088,288

(22) PCT Filed: Mar. 28, 2017

(86) PCT No.: PCT/EP2017/057301
§ 371 (c)(1),
(2) Date: Sep. 25, 2018

(87) PCT Pub. No.: WO2017/167742
PCT Pub. Date: Oct. 5, 2017

(65) Prior Publication Data
US 2019/0083064 A1    Mar. 21, 2019

Related U.S. Application Data

(60) Provisional application No. 62/315,225, filed on Mar. 30, 2016.

(51) Int. Cl.
*A61B 8/00*     (2006.01)
*G01S 15/89*    (2006.01)
(Continued)

(52) U.S. Cl.
CPC ............ *A61B 8/4488* (2013.01); *A61B 8/145* (2013.01); *A61B 8/463* (2013.01); *A61B 8/466* (2013.01);
(Continued)

(58) Field of Classification Search
CPC ....... A61B 8/4488; A61B 8/145; A61B 8/463; A61B 8/466; A61B 8/54; G01S 15/8927;
(Continued)

(56) References Cited

U.S. PATENT DOCUMENTS 4,173,007 A    10/1979  McKeighen et al.
5,060,651 A    10/1991  Kondo et al.
(Continued)

FOREIGN PATENT DOCUMENTS

EP    1214909 A1    6/2002
JP    09322896 A    12/1997
(Continued)

OTHER PUBLICATIONS

Savord et al "Fully Sampled Matrix Transducer for Real Time 3D Ultrasonic Imaging" 2003 IEEE Ultrasonics Symposium Proceedings Oct. 5-8, 2003 vol. 1, p. 945-953.

*Primary Examiner* — Patricia J Park
*Assistant Examiner* — Adil Partap S Virk (57) ABSTRACT

A diagnostic ultrasound system has a 2D array transducer which is operated with 1×N patches, patches which are only a single element wide. The "N" length of the patches extends in the elevation direction of a scanned 2D image plane, with the single element width extending in the lateral (azimuth) direction. Focusing is done along each patch in the elevation direction by a microbeamformer, and focusing in the lateral (azimuth) direction is done by the system beamformer. The minimal width of each patch in the azimuth direction enables the production of images highly resolved in the (Continued)

azimuthal plane of a 2D image, including the reception of highly resolved multilines for high frame rate imaging.

14 Claims, 7 Drawing Sheets

(51) Int. Cl.
*G01S 7/52* (2006.01)
*A61B 8/14* (2006.01)

(52) U.S. Cl.
CPC .............. *A61B 8/54* (2013.01); *G01S 7/5208* (2013.01); *G01S 15/8925* (2013.01); *G01S 15/8927* (2013.01); *G01S 7/52095* (2013.01)

(58) Field of Classification Search
CPC . G01S 7/5208; G01S 15/8925; G01S 7/52095
See application file for complete search history.

(56) References Cited

U.S. PATENT DOCUMENTS

| | | | |
|---|---|---|---|
| 5,229,933 A | 7/1993 | Larson, III | |
| 5,720,291 A | 2/1998 | Schwartz | |
| 5,997,479 A | 12/1999 | Savord et al. | |
| 6,013,032 A | 1/2000 | Savord | |
| 6,102,860 A | 8/2000 | Mooney | |
| 6,126,602 A | 10/2000 | Savord et al. | |
| 6,368,281 B1 | 4/2002 | Solomon et al. | |
| 6,375,617 B1 | 4/2002 | Fraser | |
| 6,419,633 B1 | 4/2002 | Robinson et al. | |
| 6,436,048 B1 | 8/2002 | Pesque | |
| 6,443,896 B1 | 9/2002 | Detmer | |
| 7,821,180 B2 | 10/2010 | Kunkel, III | |
| 7,927,280 B2 | 4/2011 | Davidsen | |
| 8,137,272 B2 | 3/2012 | Cooley | |
| 8,317,704 B2 | 11/2012 | Robert et al. | |
| 8,465,431 B2 | 6/2013 | Daft et al. | |
| 8,647,279 B2 | 2/2014 | Daft et al. | |
| 2003/0216645 A1 | 11/2003 | Yao et al. | |
| 2009/0099454 A1* | 4/2009 | Yao | G10K 11/346 600/459 |
| 2011/0306886 A1* | 12/2011 | Daft | A61B 8/0825 600/459 |
| 2012/0179043 A1 | 7/2012 | Kim et al. | |
| 2015/0164473 A1* | 6/2015 | Kim | G01S 15/8997 600/443 |
| 2016/0011305 A1* | 1/2016 | Koptenko | G01S 7/52047 367/7 |

FOREIGN PATENT DOCUMENTS

| | | |
|---|---|---|
| WO | 03003045 A2 | 1/2003 |
| WO | 2015115676 A1 | 8/2015 |

* cited by examiner

TWO DIMENSIONAL ULTRASONIC ARRAY TRANSDUCER WITH ONE DIMENSIONAL PATCHES

This application is the U.S. National Phase application under 35 U.S.C. § 371 of International Application No. PCT/EP2017/057301 filed on Mar. 28, 2017, which claims the benefit of U.S. Provisional Application Ser. No. 62/315,225, filed Mar. 30, 2016. These applications are hereby incorporated by reference herein.

This invention relates to medical diagnostic ultrasound systems and, in particular, to ultrasound systems with two dimensional array (matrix array) transducer probes operated with one dimensional array patches.

Ultrasonic array transducers use beamformers to transmit, receive and appropriately delay and sum the ultrasonic echo signals received from elements of the transducer array. The delays are chosen in consideration of the direction (steering) and focus depth of the beams to be formed by the beamformer. After the signals from each element have been properly delayed by a channel of the beamformer, the delayed signals are combined to form a beam of properly steered and focused coherent echo signals. During ultrasonic beam transmission, the time of actuation of individual elements is the complement of the receive delay, steering and focusing the transmit beam. The choice of delays is known to be determinable from the geometry of the array elements and of the image field being interrogated by the beams.

In a traditional ultrasound system the array transducer is located in a probe which is placed against the body of the patient during imaging and contains some electronic components such as tuning elements, switches, and amplification devices. The delaying and signal combining is performed by the beamformer which is contained in the ultrasound system mainframe, to which the probe is connected by a cable.

The foregoing system architecture for an array transducer and a beamformer suffices quite well for a one dimensional (1D) transducer array, where the number of transducer elements and the number of beamformer channels are approximately the same. When the number of transducer elements exceeds the number of beamformer channels, multiplexing is generally employed and only a subset of the total number of elements of the transducer can be connected to the beamformer at any point in time. The number of elements in a 1D array can range from less than one hundred to several hundred and the typical beamformer has 128 beamformer channels. This system architecture solution became untenable with the advent of two dimensional (2D) array transducers for two and three dimensional (3D) imaging. That is because 2D array transducers steer and focus beams in both azimuth and elevation over a volumetric region. The number of transducer elements needed for this beam formation is usually in the thousands. The crux of the problem then becomes the cable that connects the probe to the system mainframe where the beamformer is located. A cable of several thousand conductors of even the finest conductive filaments becomes thick and unwieldy, making manipulation of the probe cumbersome if not impossible.

A solution to this problem is to perform at least some of the beamforming in the probe itself, as described in U.S. Pat. No. 5,229,933 (Larson, III). In the ultrasound system shown in this patent, the beamforming is partitioned between the probe and the system mainframe. Initial beamforming of groups of elements is done in the probe, where partially beamformed sums are produced. These partially beamformed sums, being fewer in number than the number of transducer elements, are coupled to the system mainframe through a cable of reasonable dimensions, where the beamforming process is completed and the final beam produced. The partial beamforming in the probe is done by what Larson, III refers to as intragroup processors, in a microbeamformer in the form of microelectronics attached to the array transducer. See also U.S. Pat. No. 5,997,479 (Savord et al.); U.S. Pat. No. 6,013,032 (Savord); U.S. Pat. No. 6,126,602 (Savord et al.); and U.S. Pat. No. 6,375,617 (Fraser). The thousands of connections between the thousands of elements of the 2D transducer array and the microbeamformer is done at the tiny dimensions of the microcircuitry and the array pitch, while the many fewer cable connections between the microbeamformer and the beamformer of the system mainframe are done by more conventional cable technologies. Various planar and curved array formats can be used with microbeamformers such as the curved arrays shown in U.S. patent applications 60/706,190 (Kunkel) and 60/706,208 (Davidsen).

The microbeamformers shown in the above patents operate by forming partially delayed sum signals from contiguous transducer element groups referred to as "patches." The signals received by all of the elements of a patch are appropriately individually delayed by the microbeamformer, then combined into a partial sum signal. Generally the patches are formed of small two-dimensional groups of elements, such as a 4×6 group or an 8×12 group of elements. This works well for phased array operation during 3D volume scanning, enabling real time scanning of the volume. But for 2D imaging, the width of such patches can limit the resolution of the image of a scanned region. This is particularly the case when doing multiline reception to improve the frame rate of imaging. Accordingly it is desirable to be able to achieve higher frame rates through multiline reception, and to do so without compromising and, preferably, with improvement of the resolution of such 2D array transducer images.

In accordance with the principles of the present invention, a diagnostic ultrasound system is described with a 2D array transducer which is operated with 1×N patches, patches which are only a single element wide. The "N" length of the patches extends in one direction of a scanned 2D image plane (e.g., the elevation direction,) with the single element width extending in the other (e.g., lateral or azimuth) direction. Focusing is done along each patch in one direction by a microbeamformer, and focusing in the other direction is done by the system beamformer. The minimal width of each patch in the second direction enables the production of images highly resolved in the plane of a 2D image, including the reception of highly resolved multilines for high frame rate imaging.

Figure 1:
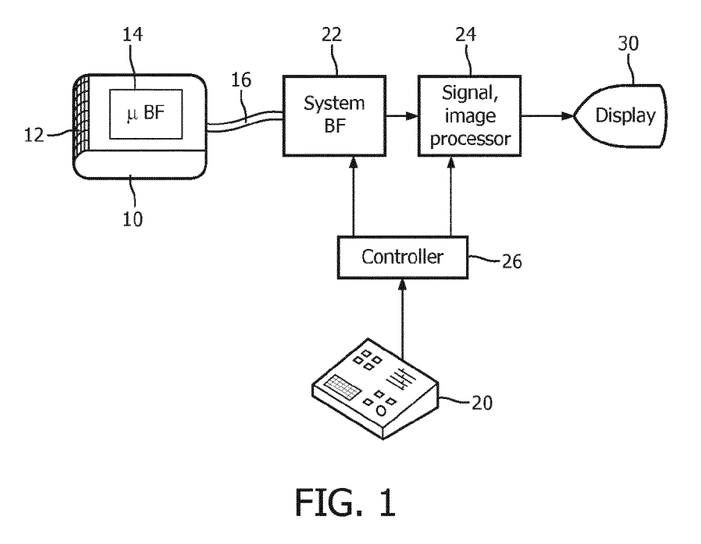
FIG. 1 illustrates in block diagram form an ultrasonic imaging system constructed in accordance with the principles of the present invention with elevation focusing performed in a microbeamformer and azimuth focusing performed in the system beamformer.

Referring first to FIG. 1, an ultrasound system constructed in accordance with the principles of the present invention is shown in block diagram form. A probe 10 has a two dimensional array transducer 12 which may be planar or curved as shown in this example. The elements of the array are coupled to a microbeamformer 14 located in the probe behind the transducer array. A microbeamformer is an integrated circuit located in the probe with beamforming channels coupled to elements of the 2D array transducer 12. The microbeamformer applies timed transmit pulses to elements of each patch of the array to transmit beams in the desired directions and to the desired focal points in the image field in front of the array. The profile of the transmit beams in the elevation dimension can exhibit a point focus, a plane wave, or any intermediate beam profile. Echoes returned by cells and tissue from the transmitted beams are received by the array elements and coupled to channels of the microbeamformer 14 where they are individually delayed. The delayed signals from a contiguous patch of transducer elements are combined to form a partial sum signal for the patch. In an analog microbeamformer implementation, combining is done by coupling the delayed signals from the elements of the patch to a common bus, obviating the need for summing circuits. The bus of each patch is coupled to a conductor of a cable 16, which conducts the partial sum patch signals to the system mainframe. In the system mainframe analog partial sum signals are digitized and coupled to channels of a system beamformer 22, which appropriately delays each partial sum signal. The delayed partial sum signals are then combined to form a coherent steered and focused receive beam. System beamformers are well known in the art and may comprise electronic hardware components, hardware controlled by software, or a microprocessor executing beamforming algorithms. In the case of a digital beamformer the beamformer includes A/D converters which convert analog signals from the microbeamformer into sampled digital echo data. The beamformer generally will include one or more microprocessors, shift registers, and or digital or analog memories to process the echo data into coherent echo signal data. Delays are effected by various means such as by the time of sampling of received signals, the write/read interval of data temporarily stored in memory, or by the length or clock rate of a shift register as described in U.S. Pat. No. 4,173,007 (McKeighen et al.) The beam signals from the image field are processed by a signal and image processor 24 to produce 2D or 3D images for display on an image display 30. The signal and image processor may comprise electronic hardware components, hardware controlled by software, or a microprocessor executing image processing algorithms. It generally will also include specialized hardware or software which processes received echo data into image data for images of a desired display format such as a scan converter.

Control of ultrasound system parameters such as probe selection, beam steering and focusing, and signal and image processing is done under control of a system controller 26 which is coupled to various modules of the system. The system controller may be formed by ASIC circuits or microprocessor circuitry and software data storage devices such as RAMs, ROMs, or disk drives. In the case of the probe 10 some of this control information is provided to the microbeamformer from the system mainframe over data lines of the cable 16, conditioning the microbeamformer for operation of the 2D array as required for the particular scanning procedure. The user controls these operating parameters by means of a control panel 20. This basic ultrasound system block diagram illustrates the partitioning of beamformation between the microbeamformer, which performs beamforming of the signals from a patch of elements, and the system beamformer which completes the beamformation process by combining the partial sum signals from the patches.

Figure 2:
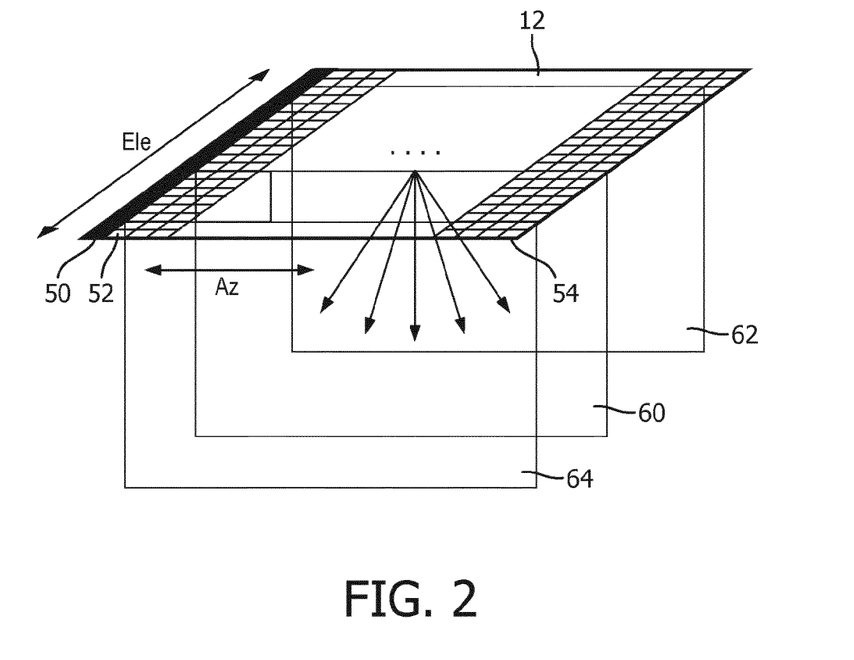
FIG. 2 illustrates the scanning of two dimensional planes by a 2D array arranged for operation with 1×N patches.

FIG. 2 illustrates a 2D array transducer 12 configured to operate in accordance with the principles of the present invention. The array 12 has M rows of elements extending in the lateral (azimuth Az.) dimension and N elements in each row extending in the elevation (Ele.) dimension. For example, an array can have 128 rows, each row having 128 elements, a total of over 16,000 elements. In accordance with the present invention, the array 12 is operated with patches 50, 52, . . . 54 that are one element wide in the azimuth direction and multiple elements long in the elevation direction, preferably N elements long, thus constituting 1×N dimensioned patches. These patches are used to transmit and receive ultrasound in order to scan image planes below the array such as the image planes 60, 62 or 64 shown in the drawing. The image planes can extend orthogonal to the plane of the 2D array as illustrated in the drawing, or be tilted at an oblique angle to the array plane. When each patch is actuated the timing of the actuation of the elements of the 1×N patch provide a desired focus in the elevation dimension, such as focusing the transmitted energy in the elevation direction along the image plane being scanned such as plane 60. Elevation focusing is administered by the microbeamformer on receive, focusing the received beam along an image plane such as image plane 60. No focusing is done in the lateral (azimuth) direction, as the patch is only one element wide in that dimension. Steering and focusing in azimuth is done by the system beamformer in the processing of partial sum signals from the patches which have been focused in elevation. Thus, the microbeamformer provides the elevation focusing and steering, whereas the azimuth focusing and steering is provided by the system beamformer. One benefit of this partitioning of the focus is that each element can be focused in elevation on the 2D image plane being scanned, resulting in good resolution in the elevation dimension. Another benefit is that the signals from each patch that are forwarded to the system beamformer for azimuth (in-plane) steering and focusing are only one element wide in the lateral dimension and the signals from each patch are unfocused in azimuth, enabling all lateral focusing to be performed by the system beamformer. This provides good in-plane lateral resolution and more highly resolved multilines when multiple lines are processed in parallel from the patch signals. The elevation focusing effected along each 1×N patch can vary from an unfocused plane wave to a sharply delineated point focus in the elevation dimension.

The effect of this partitioning of focusing between the microbeamformer 14 and the system beamformer 22 is illustrated by the delay profiles shown in FIG. 3. FIG. 3A depicts the 2D array 12 with an end 1×N patch 50 shown shaded in the drawing. The patch 50 is one element wide in the lateral dimension and extends along the full width of the array in the elevation dimension. In this example each patch of the array is focused in elevation as shown by the delay profile 70 in FIG. 3C. The wavefront from the patches is thus elevationally focused on a scan plane extending from and orthogonal to the center of the array as indicated by arrow 71 in FIG. 3C. This focusing is accomplished in this example by the delays and summing of the signals of each patch by the probe microbeamformer. In the example of a 128 by 128 element array, there are 128 partial sum signals from 128 patches oriented next to each other and extending across the lateral (azimuth) direction of the array.

The partial sum signals from the patches are coupled through the probe cable to the ultrasound system mainframe, where the beamformation process is completed by the system beamformer, which delays and sums the 128 patch signals in this example. The delay and summing by the system beamformer steers and focuses the received beam of echo signals in the lateral (azimuth) direction as illustrated by the delay profile 72 in FIG. 3D. In this example the symmetrical delay profile steers the received beam normal to the center of the array as indicated by arrow 73 in the drawing.

Figure 3A:
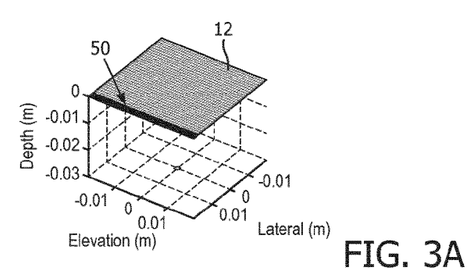
FIGS. 3A, B, C, and D illustrate the focusing of ultrasound in elevation by each 1×N patch of a 2D array and laterally by a system beamformer to produce a composite orthogonally steered and focused beam wavefront.
Figure 3B:
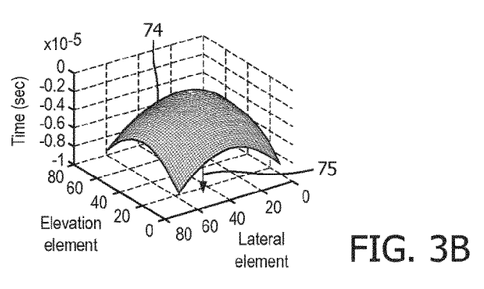
Figure 3C:
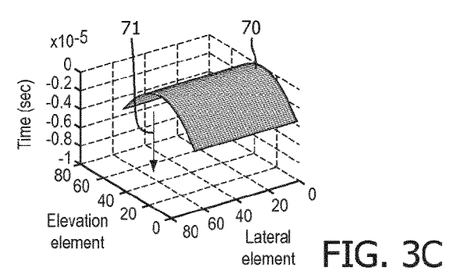
Figure 3D:
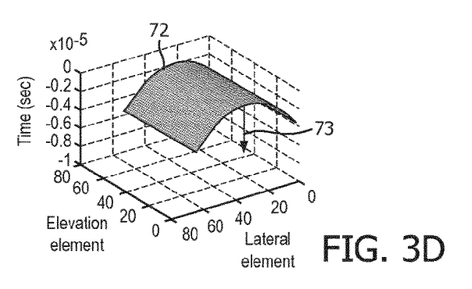
Figure 4A:
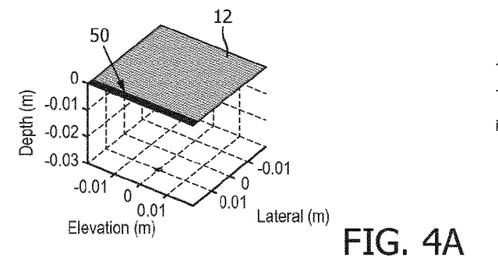
FIGS. 4A, B, C, and D illustrate the focusing of ultrasound in elevation by each 1×N patch of a 2D array and lateral steering of the wavefront by a system beamformer to produce a composite laterally steered and focused beam wavefront.
Figure 4B:
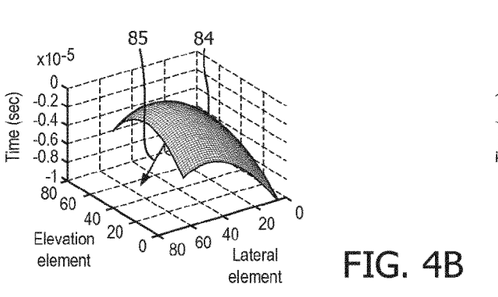
Figure 4C:
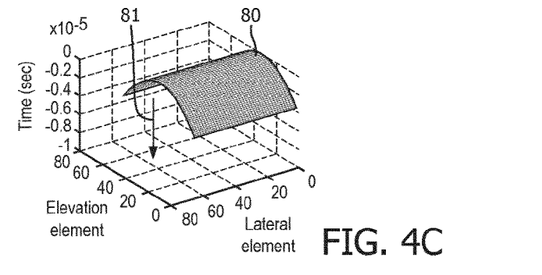
Figure 4D:
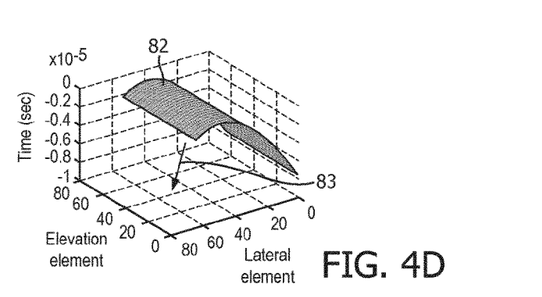

The composite delay profile 74, the combination of the elevation focusing delays effected by the microbeamformer and the in-plane (azimuth) focusing delays effected by the system beamformer, is shown in FIG. 3B. As indicated by arrow 75, the resultant beam is steered and focused orthogonal to the center of the array as a result of the symmetrical delay profiles 70 and 72 of both the elevation and lateral (azimuth) focusing delays.

FIG. 4 illustrates another example of this partitioned elevation and azimuth focusing, this time for a beam steered to the left in the azimuth plane by the delays effected by the system beamformer. FIG. 4C shows the same elevation focusing delay profile 80 as before, focused along a plane extending orthogonal to the center of the array as indicated by arrow 81. FIG. 4D shows that the delays of the system beamformer are weighted to the left, illustrated by the delay profile 82 which steers the beams to the left as indicated by arrow 83. As a result, the composite elevation and azimuth delay profile 84 directs beams along the center of the array in elevation and to the left in azimuth as indicated by arrow 85 in FIG. 4B.

Figure 5:
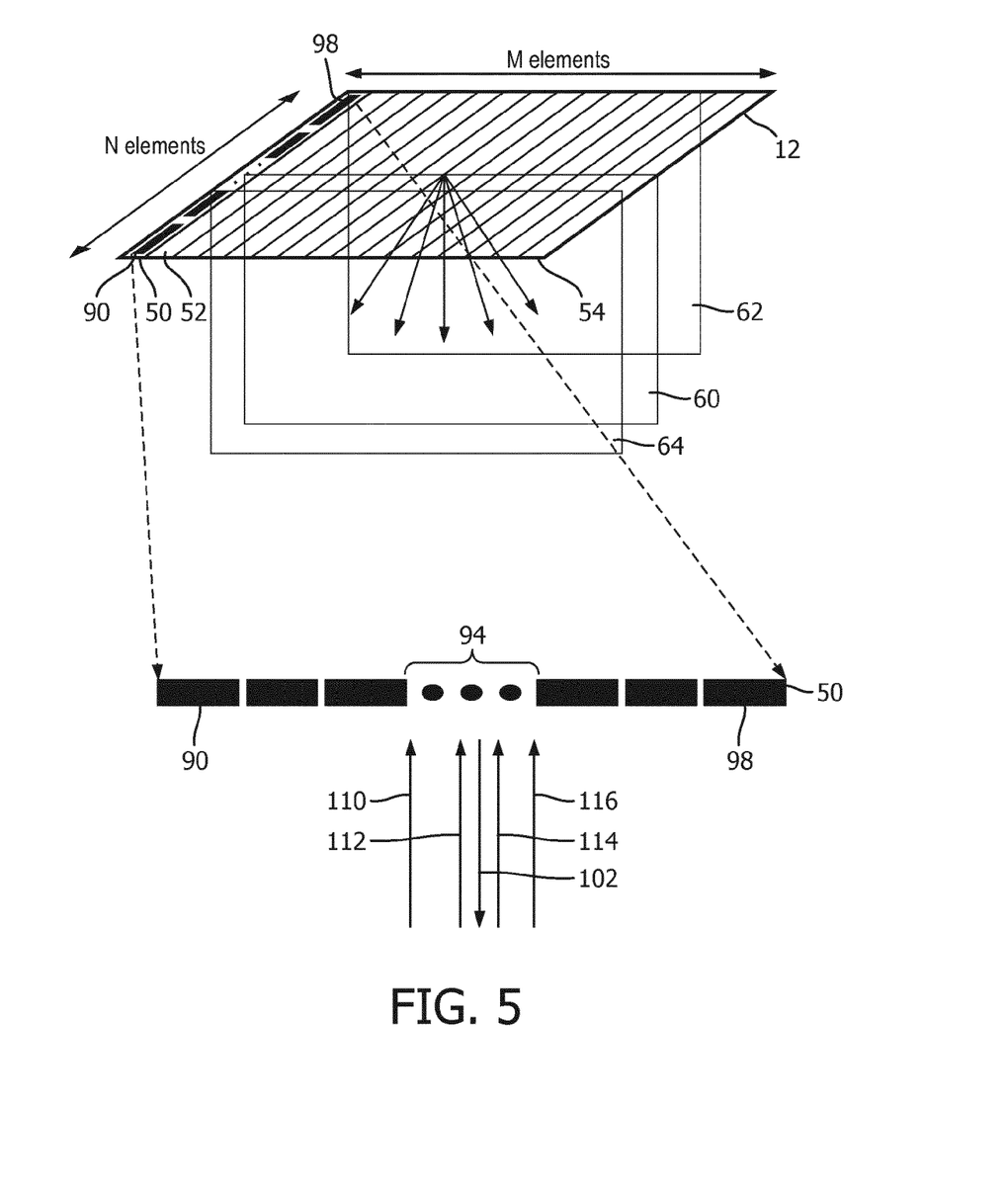
FIG. 5 illustrates an implementation of the present invention in which 1×N patches are segmented into subpatches for multiline acquisition in elevation.

FIG. 5 illustrates another implementation of 2D array operation in accordance with the present invention. In this implementation the M by N array is again segmented into 1×N patches and, in addition, each 1×N patch is further segmented into subpatches, several of which are indicated for patch 50 at 90, 94, 98. Now, in addition to being able to focus the entire patch in the elevation plane of the patch width, individual focusing can be done from each subpatch of elements. In the previous example of a 128 element by 128 element 2D array, with each 1×N patch being 128 elements long, each patch could be segmented into 8 subpatches of sixteen elements each, for instance. The subpatches can be operated to further improve the frame rate of display, particularly when performing 3D imaging. For example, three scan planes 60, 62 and 64 are shown extending into the volumetric region below the 2D array in FIG. 5. Multiple planes like these can be scanned and the echo data from all the planes used to form a 3D image of the volumetric region below the array. For example, sixty-four such planes could be scanned to gather the 3D data needed for the 3D image. With conventional scanning, this would require the acquisition time of the sixty-four planes of data, which would govern the frame rate of display. FIG. 5, however, illustrates the simultaneous acquisition of scan-lines of data 110, 112, 114 and 116 from four such planes in response to a single transmit beam 102. The delays needed to form these four multilines can be applied by the microbeamformer, or the multilines can be formed by delays applied by the system beamformer. Thus, four planes can be scanned by this multiline acquisition in the time normally required to scan one plane, increasing the frame rate of display by a factor of four.

Figure 6:
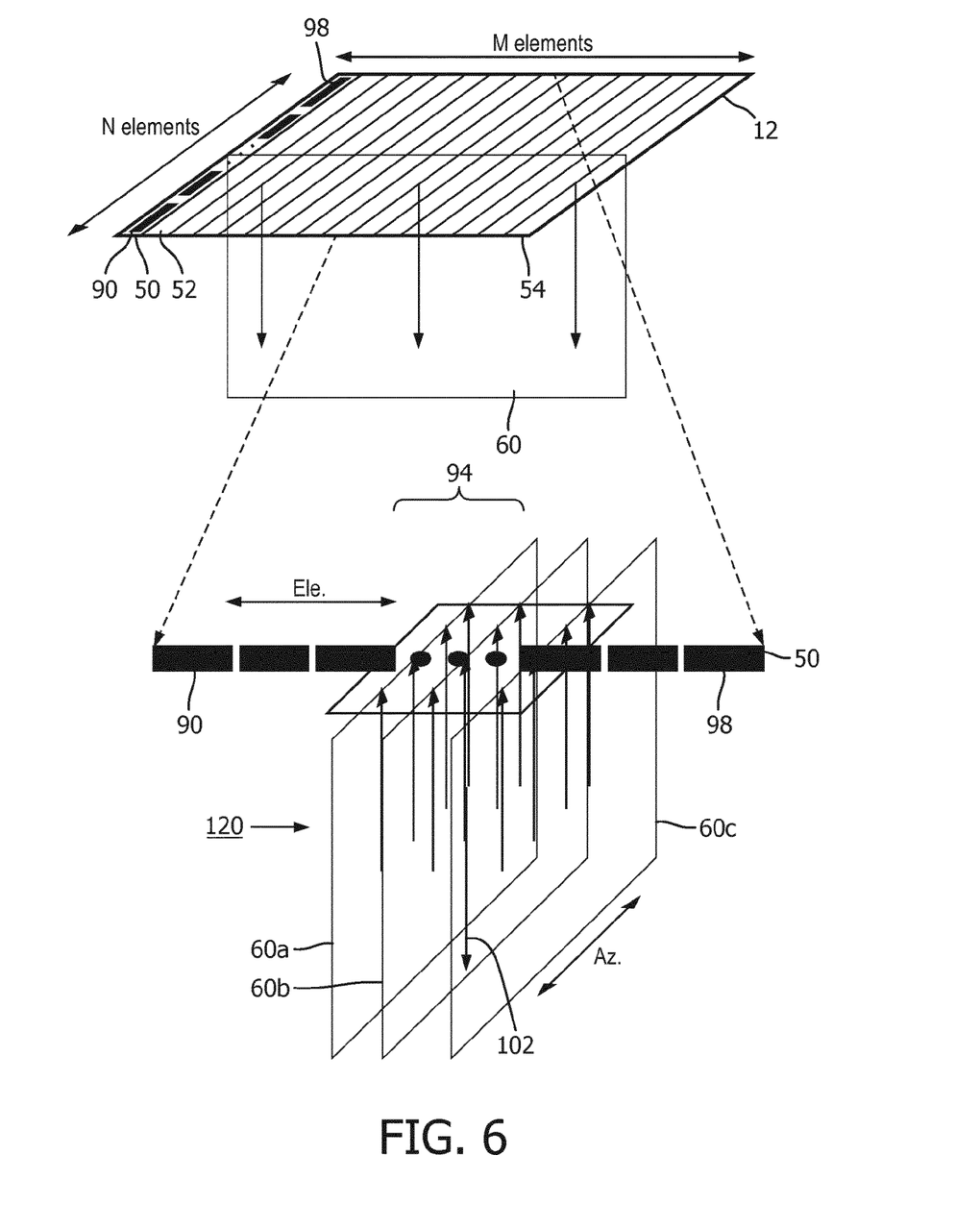
FIG. 6 illustrates an implementation of the present invention in which 1×N patches are segmented into subpatches for multiline acquisition in multiple elevation planes.

FIG. 6 illustrates another implementation of the present invention which will increase the frame rate of display for 3D imaging even further. In this example receive multilines 120 are formed around a single transmit beam 102 in both the elevation and azimuth directions. The illustration shows four multilines formed in a central scan plane 60b, four multilines formed on one parallel scan plane 60a, and four multilines formed on another parallel scan plane 60c. This affords a sixteen-fold increase in data acquisition and frame rate over conventional single-line scanning. Since the multilines extend in both the azimuth and elevation dimensions, the delays for formation of these multilines are preferably applied by the system beamformer.

Figure 7:
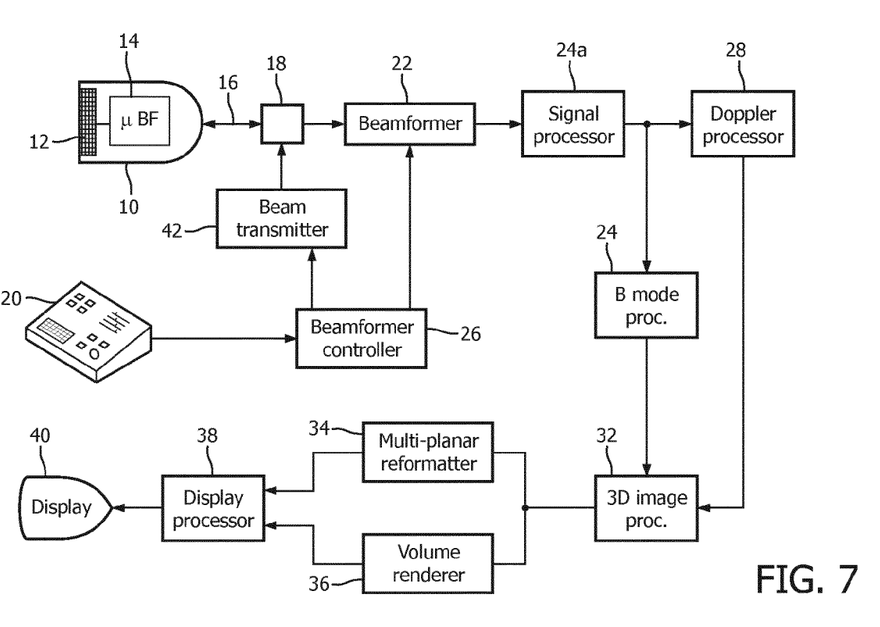
FIG. 7 illustrates in detailed block diagram form an ultrasonic imaging system constructed in accordance with the principles of the present invention.

A detailed block diagram of an ultrasound system constructed in accordance with the principles of the present invention is shown in FIG. 7. An ultrasound probe 10 includes a two dimensional array transducer 12 which transmits electronically steered and focused beams over a planar or volumetric region and receives single or multiple receive beams in response to each transmit beam. The elements of the transducer array are coupled to a microbeamformer (μBF) 14 where the elements of the array are operated in 1×N patches and subpatches as described above. The microbeamformer 12 performs partial beamforming of received echo signals in the elevation dimension and thereby reduces the number of conductors in the cable 16 between the probe 10 and the main system. Suitable two dimensional arrays are described in U.S. Pat. No. 6,419,633 (Robinson et al.) and in U.S. Pat. No. 6,368,281 (Solomon et al.) Microbeamformers are described in U.S. Pat. No. 5,997,479 (Savord et al.) and U.S. Pat. No. 6,013,032 (Savord). The transmit beam characteristics of the array are controlled by a beam transmitter 42, which causes the apodized aperture elements of the array to emit a focused beam of the desired breadth in a desired direction through a region of interest for imaging. Transmit pulses are coupled from the beam transmitter 42 to the elements of the array by means of a transmit/receive switch 18. The echo signals received by the array elements and microbeamformer in response to a transmit beam are focused in elevation by delays and summing of the 1×N patch signals in the microbeamformer and coupled to a system beamformer 22, where the partially beamformed echo signals from the microbeamformer are delayed with azimuth (laterally) computed delays and summed to form fully beamformed single or multiple receive beams in response to a transmit beam. A suitable beamformer for this purpose is described in the aforementioned Savord '032 patent.

The receive beams formed by the beamformer 22 are coupled to a signal processor 24a which performs functions such as filtering and quadrature demodulation. The echo signals of the processed receive beams are coupled to a Doppler processor 28 and/or a B mode processor 24. The Doppler processor 28 processes the echo information into Doppler power or velocity information. For B mode imaging the receive beam echoes are envelope detected and the signals logarithmically compressed to a suitable dynamic range by the B mode processor 24. The echo signals from a volumetric region are processed to form a 3D image dataset by a 3D image processor 32. The 3D image data may be processed for display in several ways. One way is to produce multiple 2D planes of the volume. This is described in U.S. Pat. No. 6,443,896 (Detmer). Such planar images of a volumetric region are produced by a multi-planar reformatter 34. The three dimensional image data may also be rendered to form a perspective or kinetic parallax 3D display by a volume renderer 36. The resulting images, which may be B mode, Doppler or both as described in U.S. Pat. No. 5,720,291 (Schwartz), are coupled to a display processor 38, from which they are displayed on an image display 40. User control of the beamformer controller 26 and other functions of the ultrasound system are provided through a user interface or control panel 20.

It should be noted that the various embodiments described above and illustrated by the exemplary ultrasound system of FIG. 1 may be implemented in hardware, software or a combination thereof. The various embodiments and/or components, for example, the modules, or components and controllers therein, also may be implemented as part of one or more computers or microprocessors. The computer or processor may include a computing device, an input device, a display unit and an interface, for example, for accessing the Internet. The computer or processor may include a microprocessor. The microprocessor may be connected to a communication bus, for example, to access a PACS system. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, solid-state thumb drive, and the like. The storage device may also be other similar means for loading computer programs or other instructions into the computer or processor.

As used herein, the term "computer" or "module" or "processor" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of these terms.

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

Furthermore, the limitations of the following claims are not written in means-plus-function format and are not intended to be interpreted based on 35 U.S.C. 112, sixth paragraph, unless and until such claim limitations expressly use the phrase "means for" followed by a statement of function devoid of further structure.

Alternate variations in implementation of the present invention will readily occur to those skilled in the art. As mentioned above, the 1×N patch orientation can be rotated by 90 o (or any other angle) such that the N dimension of the patches extends in the azimuth direction and the 1×N patches are aligned next to each other in the elevation direction. Another variation is to set the microbeamformer to apply the azimuth focus delays, while the system beamformer applies the elevation focus delays. For example, the system can be implemented with a physical or softkey switch whereby the user can select the orientation of the N dimension of the 1×N patches to be in either the elevation or azimuth direction, with the delays applied by the microbeamformer and system beamformer falling in line with the selected orientation. Such a user control can also have a third setting to select standard 2D patches to operate the 2D array and beamformers in the conventional manner for a matrix array.

What is claimed is:

1. An ultrasonic diagnostic imaging system for display of 2D or 3D images comprising:
   an ultrasound probe having a two dimensional array transducer adapted to scan a target region with 1xN patches of elements of the array, wherein N extends in a dimension of the array transducer, wherein the N dimension of the patches extends in one of an elevation or azimuth dimension, and wherein each 1×N patch is divided into subpatches comprising a plurality of elements less than the full N elements;
   a microbeamformer located in the ultrasound probe and coupled to elements of the array which applies delays to a plurality of subpatch signals received from each subpatch to focus the subpatch signals in the one of the dimensions;
   a system beamformer coupled to the ultrasound probe to receive the focused patch subpatch signals and apply delays to the subpatch signals to steer and/or focus the signals in the other of the elevation or azimuth dimensions;
   a beamformer controller, coupled to the microbeamformer and the system beamformer, and responsive to a user control to control the scanning of a target region;
   an image processor responsive to the signals steered and/or focused by the system beamformer to produce image data; and
   a display, coupled to the image processor, to display a 2D or 3D image of the target region.

2. The ultrasonic diagnostic imaging system of claim 1, wherein the microbeamformer further controls the timing of signals transmitted by each subpatch to focus the subpatch signals in the elevation dimension.

3. The ultrasonic diagnostic imaging system of claim 2, wherein the microbeamformer further controls the timing of signals transmitted by each subpatch to focus the subpatch signals at a point focus in the elevation dimension.

4. The ultrasonic diagnostic imaging system of claim 2, wherein the microbeamformer further controls the timing of signals transmitted by each subpatch to focus the subpatch signals as a plane wave in the elevation dimension.

5. The ultrasonic diagnostic imaging system of claim 1, wherein the microbeamformer applies delays to signals received from each subpatch to focus the subpatch signals at a point in the elevation dimension.

6. The ultrasonic diagnostic imaging system of claim 1, wherein the microbeamformer applies delays to signals received from each subpatch to focus the subpatch signals as a plane wave in the elevation dimension.

7. The ultrasonic diagnostic imaging system of claim 1, wherein the microbeamformer further comprises a microbeamformer circuit which applies analog delays to signals received from each subpatch.

8. The ultrasonic diagnostic imaging system of claim 7, wherein the microbeamformer focuses transmitted and/or received signals of the subpatches in the elevation dimension, and
wherein the system beamformer further comprises a digital beamformer which digitally delays the elevation focused subpatch signals.

9. The ultrasonic diagnostic imaging system of claim 1, wherein the two dimensional array transducer further comprises M rows of elements with each row comprising N elements,
wherein M extends in one of the azimuth dimension or the elevation dimension and N extends in the other of the azimuth dimension or the elevation dimension.

10. The ultrasonic diagnostic imaging system of claim 1, wherein each subpatch is a single transducer element wide in the azimuth dimension and each subpatch extends for the plurality of transducer elements in the elevation dimension.

11. The ultrasonic diagnostic imaging system of claim 1, wherein the N-dimension extends in the elevation dimension, and wherein the delays applied by the microbeamformer to signals received from each subpatch affect no focusing in the azimuth dimension.

12. The ultrasonic diagnostic imaging system of claim 1, wherein a wavefront produced by the microbeamformer delays is focused along a plane extending in the azimuth direction.

13. The ultrasonic diagnostic imaging system of claim 12, wherein a wavefront produced by the system beamformer delays is focused along a plane extending in the elevation direction.

14. The ultrasonic diagnostic imaging system of claim 1, wherein a wavefront produced by the microbeamformer and system beamformer delays is steered and focused in both azimuth and elevation.

* * * * *